(12) United States Patent
Safai

(10) Patent No.: US 8,503,610 B1
(45) Date of Patent: Aug. 6, 2013

(54) X-RAY INSPECTION TOOL

(75) Inventor: Morteza Safai, Seattle, WA (US)

(73) Assignee: The Boeing Company, Chicago, IL (US)

( * ) Notice: Subject to any disclaimer, the term of this patent is extended or adjusted under 35 U.S.C. 154(b) by 232 days.

(21) Appl. No.: 12/952,652

(22) Filed: Nov. 23, 2010

(51) Int. Cl.
*G01N 23/20* (2006.01)

(52) U.S. Cl.
USPC ............................................. 378/70; 378/86

(58) Field of Classification Search
USPC ........................................... 378/6, 70, 86, 87
See application file for complete search history.

(56) References Cited

U.S. PATENT DOCUMENTS

| | | | |
|---|---|---|---|
| 5,411,890 A | 5/1995 | Falat | |
| 5,429,009 A | 7/1995 | Wolfe et al. | |
| 5,466,605 A | 11/1995 | Glaunsinger et al. | |
| 5,482,890 A | 1/1996 | Liu et al. | |
| 6,379,622 B1 | 4/2002 | Polak et al. | |
| 6,564,620 B1 | 5/2003 | Jaeger | |
| 6,627,914 B1 | 9/2003 | Komiyama et al. | |
| 6,657,232 B2 | 12/2003 | Morkoc | |
| 6,710,366 B1 | 3/2004 | Lee et al. | |
| 6,717,664 B2 | 4/2004 | Floyd et al. | |
| 6,843,328 B2 | 1/2005 | Boyl-Davis et al. | |
| 7,002,079 B2 | 2/2006 | Mitchell et al. | |
| 7,005,669 B1 | 2/2006 | Lee | |
| 7,026,641 B2 | 4/2006 | Mohseni et al. | |
| 7,212,283 B2 | 5/2007 | Hother et al. | |
| 7,216,408 B2 | 5/2007 | Boyl-Davis et al. | |
| 7,253,004 B2 | 8/2007 | Vossmeyer et al. | |
| 7,304,305 B2 | 12/2007 | Hunt | |
| 7,306,823 B2 | 12/2007 | Sager et al. | |
| 7,342,235 B1 | 3/2008 | Harrison et al. | |
| 7,345,596 B2 | 3/2008 | Wallach et al. | |
| 7,380,776 B2 | 6/2008 | Boyl-Davis et al. | |
| 7,513,941 B2 | 4/2009 | Frey et al. | |
| 7,528,372 B2 | 5/2009 | Garvey, III et al. | |
| 7,529,343 B2 | 5/2009 | Safai et al. | |
| 7,534,489 B2 | 5/2009 | Ying et al. | |
| 7,535,990 B2 | 5/2009 | Safai et al. | |

(Continued)

FOREIGN PATENT DOCUMENTS

| | | |
|---|---|---|
| EP | 1130385 | 9/2001 |
| EP | 1245949 | 10/2002 |

(Continued)

OTHER PUBLICATIONS

Shedlock et al., "X-Ray Backscatter Imaging for Aerospace Applications", 5 pages, retrieved Nov. 23, 2010.

(Continued)

*Primary Examiner* — Jurie Yun
(74) *Attorney, Agent, or Firm* — Yee & Associates, P.C.

(57) ABSTRACT

A method and apparatus for identifying a response to a plurality of x-rays are provided. In one advantageous embodiment, an apparatus comprising a housing, an x-ray tube, an anode, and an x-ray detector are provided. The housing has a longitudinal axis. The x-ray tube is associated with the housing and configured to generate a plurality of x-rays. The anode is associated with the housing and configured to rotate around the longitudinal axis to a direction and direct the plurality of x-rays generated by the x-ray tube toward a surface of an object in the direction. The x-ray detector is associated with the housing and configured to detect a response to the plurality of x-rays reflected from the surface of the object.

20 Claims, 6 Drawing Sheets

U.S. PATENT DOCUMENTS

| | | | |
|---|---|---|---|
| 7,567,649 B1 | 7/2009 | Safai et al. | |
| 7,620,150 B1* | 11/2009 | Annis | 378/87 |
| 7,623,626 B2 | 11/2009 | Safai et al. | |
| 7,649,967 B2 | 1/2010 | Jonsson | |
| 7,649,976 B2 | 1/2010 | Georgeson et al. | |
| 7,780,913 B2 | 8/2010 | Farmer | |
| 7,785,717 B2 | 8/2010 | Barbera-Guillem | |
| 7,807,265 B2 | 10/2010 | Santra et al. | |
| 7,887,938 B2 | 2/2011 | Fristad et al. | |
| 7,902,524 B2 | 3/2011 | Safai et al. | |
| 7,925,452 B2 | 4/2011 | Safai et al. | |
| 7,955,858 B2 | 6/2011 | Davis et al. | |
| 7,976,726 B2 | 7/2011 | Wang et al. | |
| 2003/0068824 A1 | 4/2003 | Frankel et al. | |
| 2003/0109056 A1 | 6/2003 | Vossmeyer et al. | |
| 2003/0160182 A1 | 8/2003 | Petrich et al. | |
| 2004/0211894 A1 | 10/2004 | Hother et al. | |
| 2005/0109939 A1* | 5/2005 | Engler et al. | 250/336.1 |
| 2005/0200481 A1 | 9/2005 | Wallach | |
| 2006/0062902 A1 | 3/2006 | Sager et al. | |
| 2006/0068203 A1 | 3/2006 | Ying et al. | |
| 2006/0152706 A1 | 7/2006 | Butland | |
| 2007/0042139 A1 | 2/2007 | Cooper et al. | |
| 2007/0048867 A1 | 3/2007 | Farmer | |
| 2007/0110960 A1 | 5/2007 | Frey et al. | |
| 2007/0189454 A1 | 8/2007 | Georgeson et al. | |
| 2007/0194297 A1 | 8/2007 | McCarthy et al. | |
| 2007/0264719 A1 | 11/2007 | Santra et al. | |
| 2010/0151577 A1 | 6/2010 | Davis et al. | |
| 2010/0213387 A1 | 8/2010 | Safai et al. | |
| 2011/0176962 A1 | 7/2011 | Davis et al. | |
| 2012/0148026 A1 | 6/2012 | Safai | |

FOREIGN PATENT DOCUMENTS

| | | |
|---|---|---|
| WO | 9805946 A1 | 2/1998 |
| WO | 0214785 A1 | 2/2002 |
| WO | WO2005124340 | 12/2005 |
| WO | WO2006107331 | 10/2006 |
| WO | WO2006107493 | 10/2006 |
| WO | 2007130545 A2 | 11/2007 |
| WO | 2007130576 A2 | 11/2007 |
| WO | 2009055284 A1 | 4/2009 |
| WO | WO2010077930 | 7/2010 |
| WO | WO2012071118 | 5/2012 |

OTHER PUBLICATIONS

PCT Search Report dated Jan. 6, 2012 regarding International Application No. PCT/US2011/057030, filing date Oct. 20, 2011, (14 pages).

Dunn, "Flaw detection by X-ray scanning using the rolling-window template-matching procedure", Applied Radiation and Isotopes, Elsevier, vol. 61, Copyright 2004, pp. 1217-1225.

Dyba et al., "STED-Microscopy overcomes the diffraction limit in a fundamental way.", retrieved Jun. 15, 2012, 3 pages http://www3.mpibpc.mpg.de/groups/hell/STED.htm.

"Group (periodic table)", Wikipedia, retrieved Jun. 15, 2012, 3 pages http://en.wikipedia.org/wiki/Group_(periodic_table).

"Making Nanodots Useful for Chemistry", ScienceDaily, Jun. 19, 2003, retrieved Jun. 15, 2012, 2 pages http://www.sciencedaily.com/releases/2003/06/030619075658.htm.

"Single Photon Detection", Quantum Information Group, Toshiba Research Europe Ltd., Cambridge Research Laboratory, retrieved Jun. 15, 2012, 2 pages http://www.toshiba-europe.com/research/crl/qig/singlephotondetection.html.

Westphal et al., "Nanoscale Resolution in the Focal Plane of an Optical Microscope", Physical Review Letters, The American Physical Society, Apr. 2005, 4 pages.

"[3-(2-Aminoethyl)aminopropyl]trimethoxysilane", ScienceLab, retrieved Jun. 15, 2012, 2 pages http://www.sciencelab.com/page/S/PVAR/SLA3115.

PCT Search Report dated Mar. 31, 2010 regarding international application No. PCT/US2009/068223, applicant The Boeing Company, 5 pages.

PCT Search Report dated Jan. 19, 2012 regarding international application No. PCT/US2011/057892, applicant The Boeing Company, 5 pages.

USPTO Office Action dated Feb. 10, 2012 for U.S. Appl. No. 13/070,046, 17 pages.

USPTO Office Action dated Sep. 22, 2011 for U.S. Appl. No. 13/070,046, 15 pages.

USPTO Final Office Action dated Aug. 5, 2010 for U.S. Appl. No. 12/335,724, 10 pages.

USPTO Office Action dated Oct. 28, 2009 for U.S. Appl. No. 12/335,724, 18 pages.

USPTO Office Action dated Feb. 8, 2011 for U.S. Appl. No. 12/335,724, 8 pages.

USPTO Office Action dated Mar. 9, 2010 for U.S. Appl. No. 12/335,724, 7 pages.

USPTO Notice of Allowance dated Mar. 25, 2011 for U.S. Appl. No. 12/335,724, 5 pages.

USPTO Pre-Brief Appeal Conference Decision dated Dec. 1, 2010 for U.S. Appl. No. 12/335,724, 2 pages.

USPTO Office Action dated Aug. 20, 2010 for U.S. Appl. No. 12/390,965, 15 pages.

USPTO Notice of Allowance dated Nov. 3, 2010 for U.S. Appl. No. 12/390,965, 7 pages.

Safai, "Quantum Dot Detection", U.S. Appl. No. 13/226,750, filed Sep. 7, 2011, 45 pages.

Artemyev et al., "Quantum dots in photonic dots," Applied Physics Letters, vol. 96, Issue 11, Mar. 2000, pp. 1353-1355.

Bakkers et al., "Excited-State Dynamics in CdS Quantum Dots Absorbed on a Metal Electrode," Journal of Physical Chemistry, vol. 103, No. 14, Mar. 1999, pp. 2781-2788.

Bryant et al., "The use of fluorescent probes for the detection of under-film corrosion," Progress in Organic Coatings, vol. 57, Issue 4, Dec. 2006, pp. 416-420.

Hakim et al., "Nanocoating Individual Silica Nanoparticles by Atomic Layer Deposition in a Fluidized Bed Reactor," Chemical Vapor Deposition, vol. 11, Issue 10, Oct. 2005, pp. 420-425.

Yu et al., "Experimental determination of the extinction coefficient of CdTe, CdSe, and CdS nanocrystals," Chemistry of Materials, vol. 15, No. 14, Jun. 2003, pp. 2854-2860.

Final office action dated Jul. 3, 2012 regarding U.S. Appl. No. 13/070,046, 10 pages.

Talion et al., "X-ray Backscatter Imaging for Aerospace Applications," Nucsafe,Inc., Scatter X-ray Imaging, Boeing Research & Technology presentation, Jul. 2010, 24 pages.

"Advantages of quantum dots over conventional fluorophores," UCI web site, Jun. 2007, 2 pages, accessed Jan. 15, 2013 http://bme240.eng.uci.edu/students/07s/yokabe/advantages.htm (referenced by examiner Jul. 3, 2012 in final office action).

Notice of allowance dated Dec. 14, 2012 regarding U.S. Appl. No. 12/965,159, 22 pages.

* cited by examiner

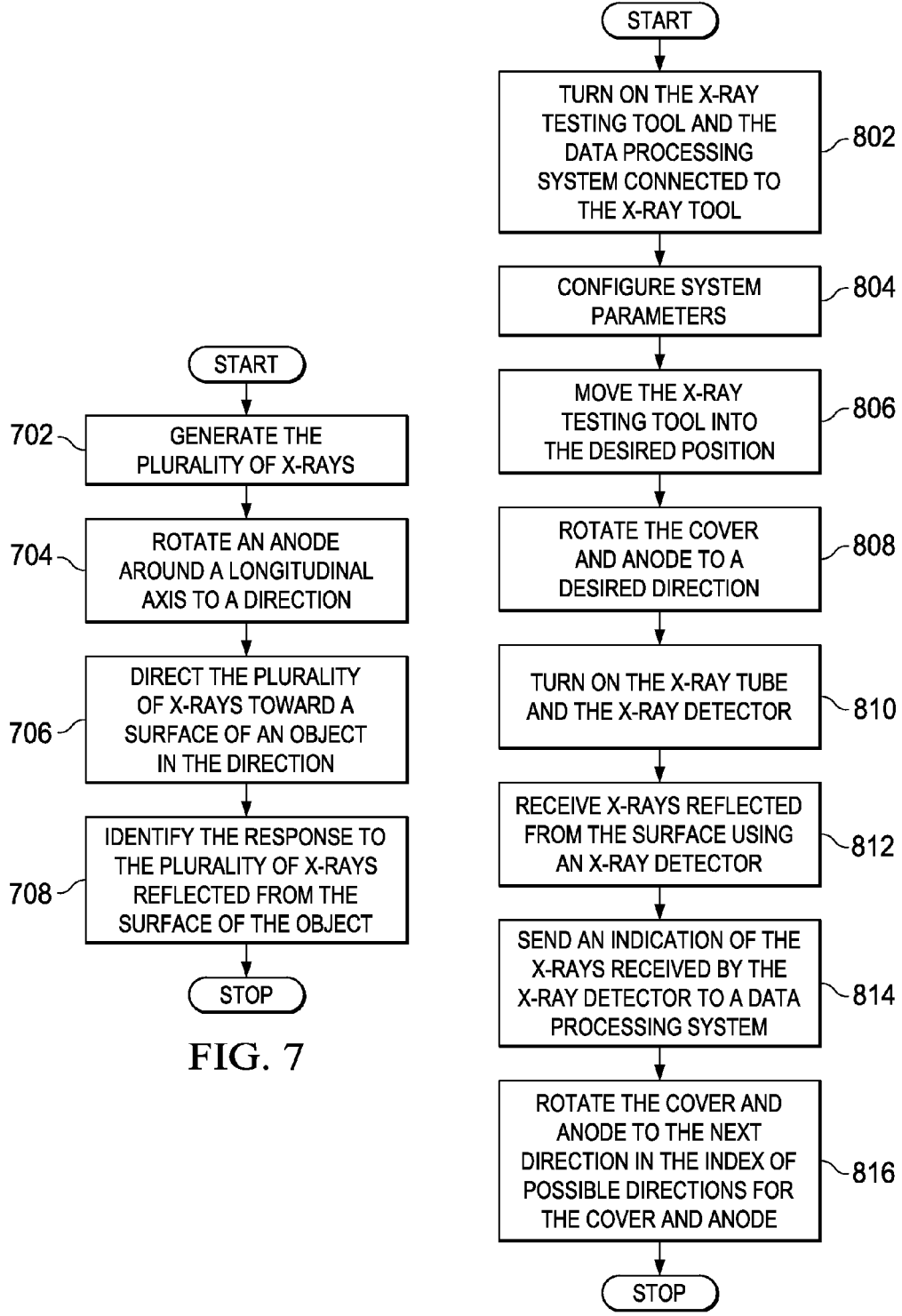

X-RAY INSPECTION TOOL

BACKGROUND INFORMATION

1. Field

The present disclosure relates generally to x-ray systems and more specifically to a method and apparatus for identifying a number of x-rays.

2. Background

X-rays are frequently used to generate images of a surface. X-rays are generated by an x-ray tube and directed at the surface. Some of the x-rays are reflected by the surface, while other x-rays are absorbed. The x-rays that are scattered are frequently scattered by non metallic surfaces. The x-rays that are absorbed are frequently absorbed by metallic surfaces. The reflected x-rays may be collected to generate an image of the surface.

X-rays may also be used to identify inconsistencies in a surface. For example, x-rays may be generated by an x-ray tube and directed at a metallic surface to identify leaks or dings in the metallic surface. One example of a metallic surface is a storage tank.

As the x-rays contact the metallic surface, an x-ray detector located on the opposite side of the surface may receive x-rays that travel through the metallic surface to the opposite side of the surface. In the event that the x-rays contact an inconsistency in the metal surface, some of the x-rays may be allowed to pass through the surface and be received by the x-ray detector. Thus, the x-rays that contact the inconsistency are collected and the inconsistency is visible in the generated image.

In some examples, the surface may be located in an enclosed area. An enclosed area is an area that has no entrance through which an x-ray tube and/or x-ray detector may be inserted. Alternatively, the enclosed area may have an entrance, but the entry is smaller than the size of the x-ray tube and/or the x-ray detector. Thus, a portion of a structure containing the surface may be disassembled to allow access to the structure.

For example, when maintenance operations are performed, inspection of different portions of an aircraft may be performed. This inspection may include generating images of different surfaces on the aircraft. These surfaces may include the surface of an interior of a fuel tank. With a fuel tank, access panels and other suitable components of an aircraft may be disassembled in order to gain access to the inside of a fuel tank. After the inspection occurs, the different parts may be reassembled or other operations may be performed on the fuel tank. These operations may increase the time and expense needed to perform maintenance operations.

Accordingly, it would be advantageous to have a method and apparatus which takes into account one or more of the issues discussed above, as well as possibly other issues.

SUMMARY

A method and apparatus for identifying a response to a plurality of x-rays are provided. In one advantageous embodiment, an apparatus comprising a housing, an x-ray tube, an anode, and an x-ray detector are provided. The housing has a longitudinal axis. The x-ray tube is associated with the housing and configured to generate a plurality of x-rays. The anode is associated with the housing and configured to rotate around the longitudinal axis to a direction and direct the plurality of x-rays generated by the x-ray tube toward a surface of an object in the direction. The x-ray detector is associated with the housing and configured to detect a response to the plurality of x-rays reflected from the surface of the object.

In another advantageous embodiment, a method for identifying a response to a plurality of x-rays is provided. The plurality of x-rays are generated. An anode is rotated around a longitudinal axis to a direction. The plurality of x-rays are directed, by the anode, toward a surface of an object in the direction. The response to the plurality of x-rays reflected from the surface of the object is identified.

In yet another advantageous embodiment, an apparatus is provided. The apparatus comprises a housing, an x-ray tube, anode, a hole, and an x-ray detector. The housing has a longitudinal axis and configured to travel along a surface. The x-ray tube is associated with the housing and configured to generate a plurality of x-rays. The anode is associated with the housing and configured to rotate around the longitudinal axis to a direction and reflect the plurality of x-rays generated by the x-ray tube toward a surface in the direction. The hole is associated with the housing. The hole rotates with the anode around the longitudinal access and passes the plurality of x-rays reflected by the anode in the direction. The x-ray detector associated with the housing and configured to identify a response to the plurality of x-rays reflected from the surface.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

FIG. 7 depicts a flowchart of a process for identifying a response to a plurality of x-rays in accordance with an advantageous embodiment; and FIG. 8 depicts an illustration of a flowchart of a process for identifying an inconsistency in a surface of an object in accordance with an advantageous embodiment.

DETAILED DESCRIPTION

Figure 1:
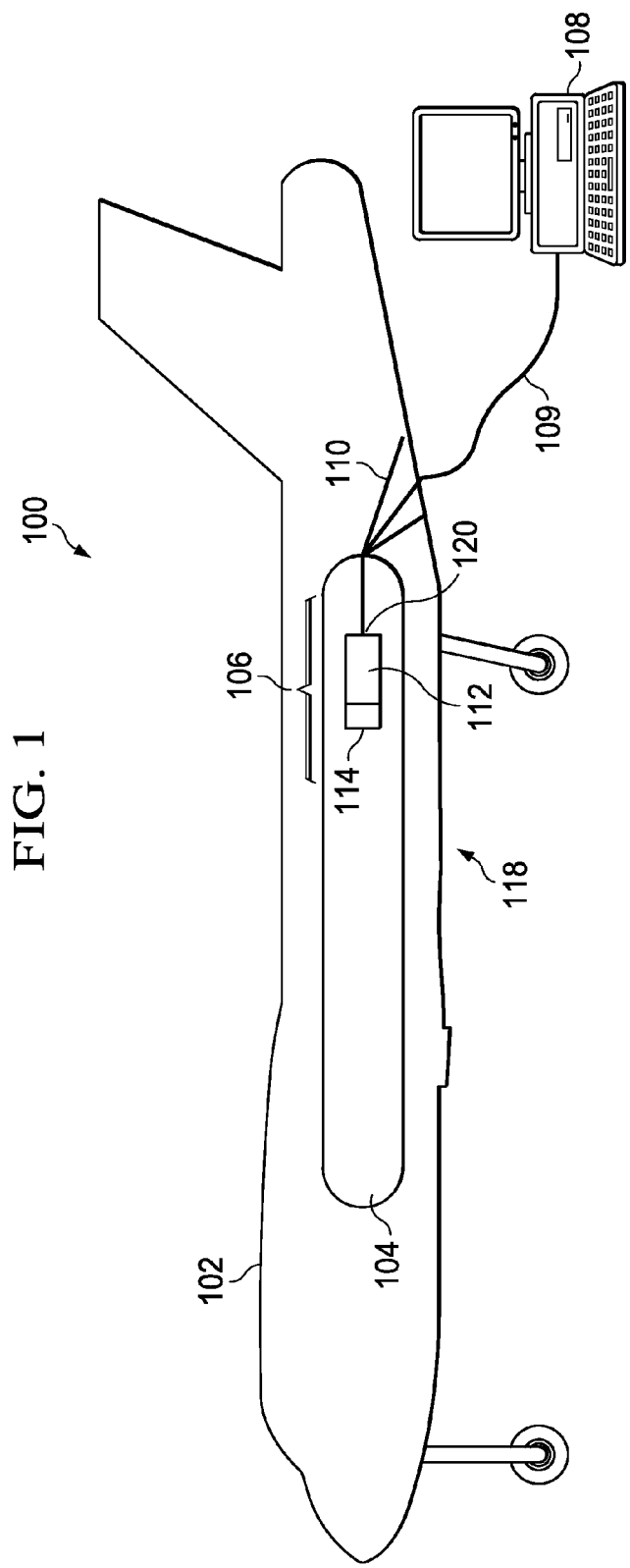
FIG. 1 depicts an illustration of an x-ray inspection environment in accordance with an advantageous embodiment.

Turning now to the figures, and more specifically to FIG. 1, an illustration of an x-ray inspection environment is depicted in accordance with an advantageous embodiment. X-ray inspection environment 100 is an example of one environment in which advantageous embodiments may be implemented.

X-ray inspection environment 100 contains aircraft 102. As depicted, aircraft 102 contains fuel tank 104. Fuel is not currently present in fuel tank 104. X-ray inspection tool 106 is also present in X-ray inspection environment 100. X-ray inspection tool 106 communicates with data processing system 108 using cable 109. Of course, in other advantageous embodiments, x-ray inspection tool 106 communicates with data processing system 108 using a wireless link.

X-ray inspection tool 106 is inserted into fuel tank 104 through opening 110. Opening 110 may be a fueling port for fuel tank 104. X-ray inspection tool 106 may have an imaging system in some advantageous embodiments. The imaging system may generate imaging data presented using data processing system 108. The imaging system may consist of one or more cameras that generate video of the environment surrounding x-ray inspection tool 106. The video may be used by an operator to move x-ray inspection tool 106 into a desired position in fuel tank 104.

Once x-ray inspection tool 106 is placed into the desired position within fuel tank 104, data processing system 108 causes x-ray inspection tool 106 to generate x-rays. In these illustrative examples, x-ray inspection tool 106 may generate x-rays using an x-ray tube. A rotating anode (not shown) inside x-ray inspection tool 106 rotates to direction 112 such that the x-rays are directed in direction 112.

X-rays contact fuel tank 104 at location 118. Since fuel tank 104 consists of a metallic surface, x-rays that contact fuel tank 104 at location 118 are reflected off location 118 toward x-ray inspection tool 106. X-rays traveling toward x-ray inspection tool 106 contact x-ray detector 120 to form a response.

X-ray detector 120 is a flexible material that wraps around the circumference of at least portion of x-ray inspection tool 106. X-ray detector 120 generates an electrical signal when the x-rays reflected from location 118 contact x-ray detector 120.

In other advantageous embodiments, however, x-ray detector 120 is a scintillator. A scintillator is a material that generates visible light in response to receiving x-rays. The scintillator may consist of an organic material. In such advantageous embodiments, x-ray detector also consists of a light sensor that identifies visible light generated by the scintillator.

X-ray detector 120 identifies that x-rays have contacted x-ray detector 120. X-ray inspection tool 106 sends an indication that x-rays were received to data processing system 108 as imaging data. Data processing system 108 receives the imaging data and direction 118 for the imaging data.

Once data processing system 108 receives the imaging data and direction 118, x-ray inspection tool 106 causes the anode and cover 114 to rotate to a second direction. X-ray inspection tool 106 repeats the generation of x-rays, direction of x-rays, and receiving of the response for the second direction. X-ray inspection tool 106 then sends imaging data for the second direction to data processing system 108.

Data processing system 108 uses the imaging data for direction 118 and the second direction to generate a flat image of fuel tank 104. The flat image may be generated by mapping direction 118 and the second direction to coordinates and combining the imaging data for direction 118 and the second direction at the coordinates.

The different advantageous embodiments recognize and take into account a number of different considerations. For example, the different advantageous embodiments recognize that testing a surface for inconsistencies is desirable. For example, an inconsistency in a surface of an object may cause the object to not perform properly or not perform for the intended purpose of the object. For example, a wheel with an inconsistency may be unable to retain air pressure for a desired period of time.

However, such a surface may be located within a structure that is difficult and time-consuming to disassemble. For example, the surface may be the inside of a fuel tank located within an aircraft. Disassembly of the aircraft in order to access the inside of the fuel tank for inspection and testing may be costly and time-consuming. The fuel tank may be tested for inconsistencies, such as leaks, dents, or other suitable inconsistencies. Once the inconsistencies are identified and located, the inconsistencies may be repaired during a maintenance operation.

The different advantageous embodiments also recognize that even when a surface may be accessed for testing and inspection, the opposite side of the surface may be difficult or time-consuming to access. The opposite side of the surface is used to position an x-ray detector such that an inconsistency in the surface would allow x-rays to pass through the surface and be received by the x-ray detector.

Additionally, the different advantageous embodiments recognize and take into account that some objects may not be disassembled for testing and inspection. For example, a pipe may not be disassembled for inspection and testing of the interior surface of the pipe.

The different advantageous embodiments identify the response to x-rays using x-ray backscattering for inspection and testing of a surface using only one side of the surface. Backscattering is a process in which x-rays are projected at a surface and the response from the surface is identified. The response may consist of reflected x-rays from the surface.

Thus, the different advantageous embodiments provide a method and apparatus for identifying a response to a plurality of x-rays. In one advantageous embodiment, an apparatus comprising a housing, an x-ray tube, an anode, and an x-ray detector are provided. The housing has a longitudinal axis. The x-ray tube is associated with the housing and configured to generate a plurality of x-rays. The anode is associated with the housing and configured to rotate around the longitudinal axis to a direction and direct the plurality of x-rays generated by the x-ray tube toward a surface of an object in the direction. The x-ray detector is associated with the housing and configured to detect a response to the plurality of x-rays reflected from the surface of the object.

Figure 2:
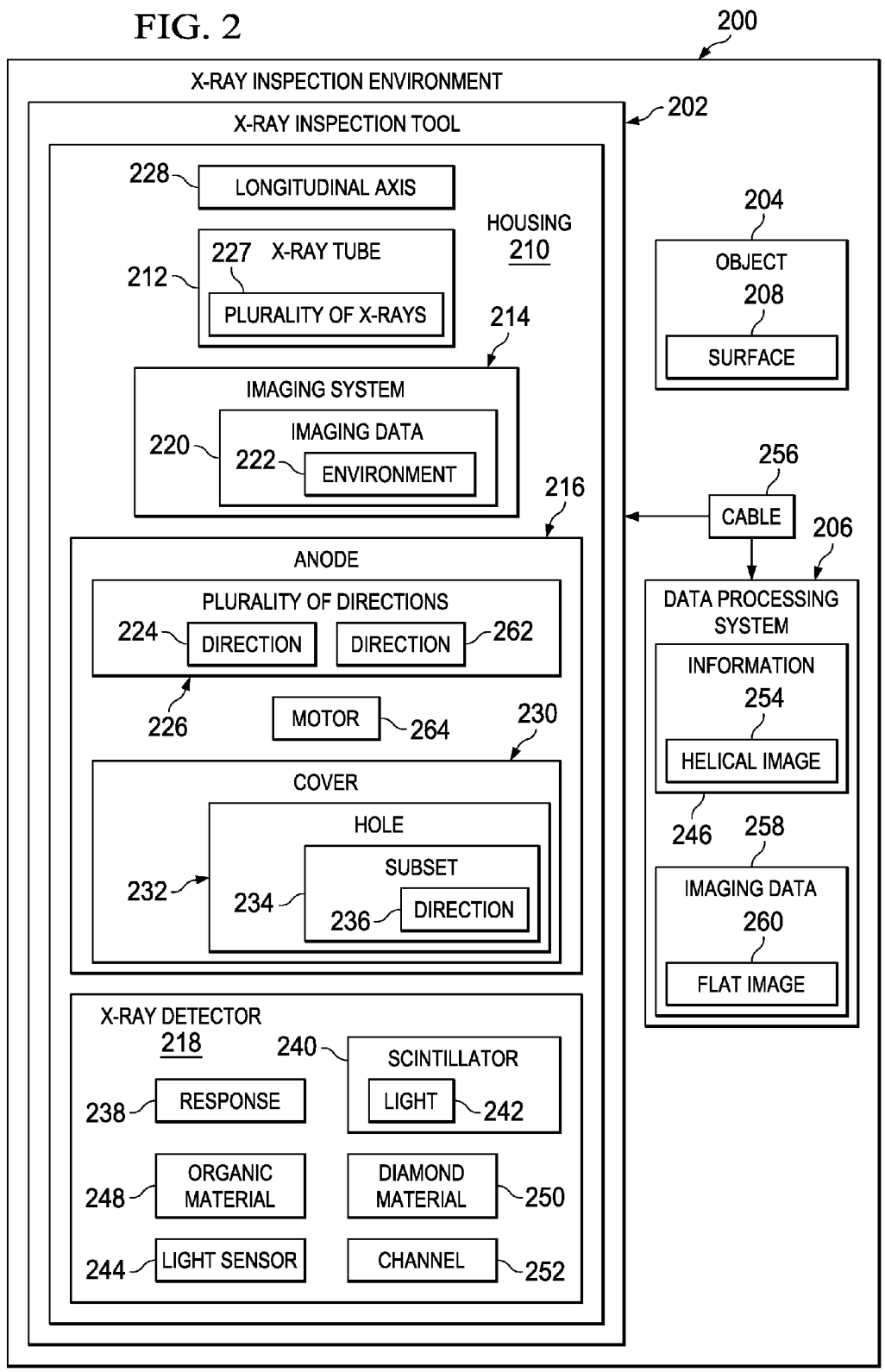
FIG. 2 depicts an illustration of a block diagram for an x-ray inspection environment in accordance with an advantageous embodiment.

Looking now to FIG. 2, an illustration a block diagram for an x-ray inspection environment is depicted in accordance with an advantageous embodiment. X-ray inspection environment 100 in FIG. 1 is an example implementation of x-ray inspection environment 200.

X-ray inspection environment 200 contains x-ray inspection tool 202, object 204 and data processing system 206. X-ray inspection tool 202 and data processing system 206 are used for identifying inconsistencies in surface 208 of object 204 in these illustrative examples.

X-ray inspection tool 202 is positioned within object 204. In some illustrative embodiments, x-ray inspection tool 202 is positioned by an operator in object 204. However, in other advantageous embodiments, x-ray inspection tool 202 is positioned using a propulsion system. The propulsion system may be, for example, an engine that moves wheels and/or a track system.

In some advantageous embodiments, x-ray inspection tool 202 has imaging system 214. Imaging system 214 generates imaging data 220 about environment 222. Imaging data 220 is photo and/or video of environment 222. Environment 222 is the environment surrounding x-ray inspection tool 202. For example, environment 222 may be the interior of object 204. Imaging system 214 uses natural, artificial, visible, infrared, and/or another suitable type of light to generate imaging data 220. Imaging data 220 may be presented using data processing system 206 and may be used to aid in positioning x-ray inspection tool 202 within object 204.

In this advantageous embodiment, the components of x-ray inspection tool 202 are located within housing 210. More specifically, housing 210 contains x-ray tube 212, imaging system 214, anode 216, and x-ray detector 218. Once x-ray inspection tool 202 is positioned in object 204 within a particular distance of surface 208, anode 216 is rotated to direction 224 along longitudinal axis 228. Longitudinal axis 228 extends through the length of housing 210 in these illustrative examples.

Direction 224 is a direction in plurality of directions 226. Plurality of directions 226 is predetermined degrees of rotation for anode 216. For example, plurality of directions 226 may consist of 20 different degrees of rotation for anode 216. By rotating anode 216, x-ray inspection tool 202 may be used to identify inconsistencies in surface 208 when surface 208 surrounds x-ray inspection tool 202.

Once anode 216 is rotated to direction 224, x-ray tube 212 generates plurality of x-rays 227. X-ray tube 212 is a microfocus x-ray tube in these examples. Plurality of x-rays 227 is electromagnetic radiation with a wavelength of about 0.01 nanometers to about 10 nanometers. Plurality of x-rays 227 is generated by colliding high velocity electrons with anode 216. In some advantageous embodiments, cover 230 is used to focus plurality of x-rays 227.

In some advantageous embodiments, hole 232 is present in cover 230 in these examples. Cover 230 rotates with anode 216 such that hole 232 is in direction 224. Hole 232 focuses plurality of x-rays 227 such that only subset 234 of plurality of x-rays 227 are allowed to pass through hole 232. Subset 234 of plurality of x-rays 227 is the x-rays in plurality of x-rays 227 that are traveling in direction 224. X-rays traveling in direction 236 are inhibited from traveling outside housing 210.

Once subset 234 of plurality of x-rays 227 pass through hole 232, subset 234 of plurality of x-rays 227 travel to surface 208. Once subset 234 of plurality of x-rays 227 reach surface 208, subset 234 may be reflected back toward x-ray inspection tool 202. In the event that an inconsistency is present in surface 208, subset 234 may not be reflected back toward x-ray inspection tool 202. For example, subset 234 may be reflected in another direction or not reflected.

In this illustrative example, an inconsistency in surface 208 is not present. Thus, subset 234 of plurality of x-rays 227 arrive at x-ray detector 218 as response 238. Response 238 consists of the x-rays that returned to x-ray detector 218 from surface 208.

X-ray detector 218 consists of scintillator 240 in some advantageous embodiments. Scintillator 240 is a material that fluoresces in response to contacting subset 234 of plurality of x-rays 227. In other words, scintillator 240 generates light 242 responsive to contacting subset 234 of plurality of x-rays 227. Light sensor 244 then identifies light 242 generated by scintillator 240 and sends information 246 about response 238 to data processing system 206. Information 246 may include an image of response 238. The image of response 238 may be helical image 254. Helical image 254 is an image that is part of a collection of images that form a coil in three dimensional space.

In other advantageous embodiments, x-ray detector 218 is comprised of organic material 248. In these illustrative examples, organic material 248 is a material that generates an electrical signal in response to contact with subset 234 of plurality of x-rays 227. The electrical signal is identified as the reflection of x-rays for direction 224 and an indication of the reflection is sent to data processing system 206 with direction 224. The indication of the reflection may be in the form of information 246.

In some advantageous embodiments, x-ray detector 218 may be covered with diamond material 250. Diamond material 250 allows x-ray detector to contact surface 208 with a force during the positioning of x-ray inspection tool 202 without negatively impacting the functionality of x-ray detector 218. Additionally, in some advantageous embodiments, x-ray detector 218 is wrapped around housing 210. In such an advantageous embodiment, x-ray detector 218 forms channel 252 through x-ray detector. Channel 252 may contain a portion of housing 210 and x-ray tube 212.

Data processing system may receive information 246 and direction 224 from x-ray inspection tool 202 using cable 256. Data processing system uses information 246 and direction 224 to generate imaging data 258. Imaging data 258 consists of flat image 260 representing a two dimensional view of helical image 254 in these examples. Of course, imaging data 258 may also be a video.

X-ray inspection tool 202 then uses motor 264 to rotate anode 216 to direction 262 in plurality of directions 226 and generates plurality of x-rays 227 again. Once response 238 is received for direction 262, x-ray inspection tool 202 sends information 246 to data processing system 206. For each information 246 received for each direction 262 in plurality of directions 226, data processing system 206 adds information 246 to imaging data 258. In these examples, data processing system adds each helical image 254 to flat image 260 using coordinates representing direction 224 and direction 262. Thus, flat image 260 contains response 238 for each direction in plurality of directions 226.

The illustration of x-ray inspection environment 200 in FIG. 2 is not meant to imply physical or architectural limitations to the manner in which different advantageous embodiments may be implemented. Other components in addition and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, x-ray inspection tool 202 may send data to data processing system 206 and receive data from data processing system 206 using a wireless link instead of cable 256. In such advantageous embodiments, such a wireless link would allow communication without the use of cable 256. Additionally, imaging data 258 may be generated once for a particular portion of surface 208. Alternatively, imaging data 258 may be updated continuously such that x-ray inspection tool 202 continues to cause data processing system 206 to update imaging data 258 by rotating anode 216 to each of plurality of directions 226 and generating plurality of x-rays 227.

Figure 3:
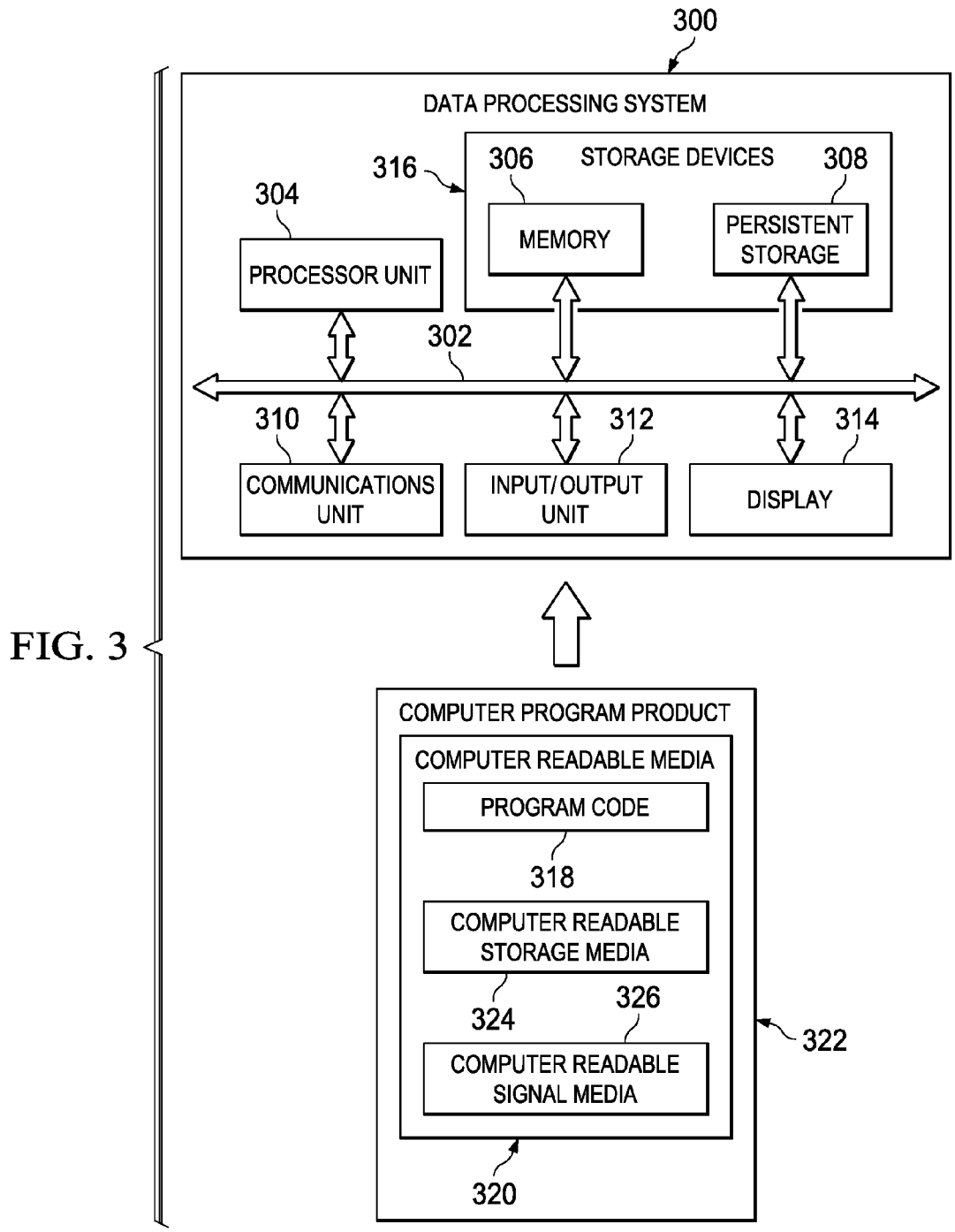
FIG. 3 depicts an illustration of a data processing system in accordance with an advantageous embodiment.

Turning now to FIG. 3, an illustration of a data processing system is depicted in accordance with an advantageous embodiment. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a number of processors, a multi-processor core, or some other type of processor, depending on the particular implementation. A number, as used herein with reference to an item, means one or more items. Further, processor unit 304 may be implemented using a number of heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices 316. A storage device is any piece of hardware that is capable of storing information, such as, for example, without limitation, data, program code in functional form, and/or other suitable information either on a temporary basis and/or a permanent basis. Storage devices 316 may also be referred to as computer readable storage devices in these examples. Memory 306, in these examples, may be, for example, a random access memory or any other suitable volatile or non-volatile storage device. Persistent storage 308 may take various forms, depending on the particular implementation.

For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard, a mouse, and/or some other suitable input device. Further, input/output unit 312 may send output to a printer. Display 314 provides a mechanism to display information to a user.

Instructions for the operating system, applications, and/or programs may be located in storage devices 316, which are in communication with processor unit 304 through communications fabric 302. In these illustrative examples, the instructions are in a functional form on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or computer readable storage media, such as memory 306 or persistent storage 308.

Program code 318 is located in a functional form on computer readable media 320 that is selectively removable and may be loaded onto or transferred to data processing system 300 for execution by processor unit 304. Program code 318 and computer readable media 320 form computer program product 322 in these examples. In one example, computer readable media 320 may be computer readable storage media 324 or computer readable signal media 326. Computer readable storage media 324 may include, for example, an optical or magnetic disk that is inserted or placed into a drive or other device that is part of persistent storage 308 for transfer onto a storage device, such as a hard drive, that is part of persistent storage 308. Computer readable storage media 324 also may take the form of a persistent storage, such as a hard drive, a thumb drive, or a flash memory, that is connected to data processing system 300. In some instances, computer readable storage media 324 may not be removable from data processing system 300. In these illustrative examples, computer readable storage media 324 is a non-transitory computer readable storage medium.

Alternatively, program code 318 may be transferred to data processing system 300 using computer readable signal media 326. Computer readable signal media 326 may be, for example, a propagated data signal containing program code 318. For example, computer readable signal media 326 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 318 may be downloaded over a network to persistent storage 308 from another device or data processing system through computer readable signal media 326 for use within data processing system 300. For instance, program code stored in a computer readable storage medium in a server data processing system may be downloaded over a network from the server to data processing system 300. The data processing system providing program code 318 may be a server computer, a client computer, or some other device capable of storing and transmitting program code 318.

The different components illustrated for data processing system 300 are not meant to provide architectural limitations to the manner in which different embodiments may be implemented. The different advantageous embodiments may be implemented in a data processing system including components in addition to or in place of those illustrated for data processing system 300. Other components shown in FIG. 3 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 304 may take the form of a hardware unit that has circuits that are manufactured or configured for a particular use. This type of hardware may perform operations without needing program code to be loaded into a memory from a storage device to be configured to perform the operations.

For example, when processor unit 304 takes the form of a hardware unit, processor unit 304 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 318 may be omitted because the processes for the different embodiments are implemented in a hardware unit.

In still another illustrative example, processor unit 304 may be implemented using a combination of processors found in computers and hardware units. Processor unit 304 may have a number of hardware units and a number of processors that are configured to run program code 318. With this depicted example, some of the processes may be implemented in the number of hardware units, while other processes may be implemented in the number of processors.

As another example, a storage device in data processing system 300 is any hardware apparatus that may store data. Memory 306, persistent storage 308, and computer readable media 320 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 306, or a cache, such as found in an interface and memory controller hub that may be present in communications fabric 302.

Figure 4:
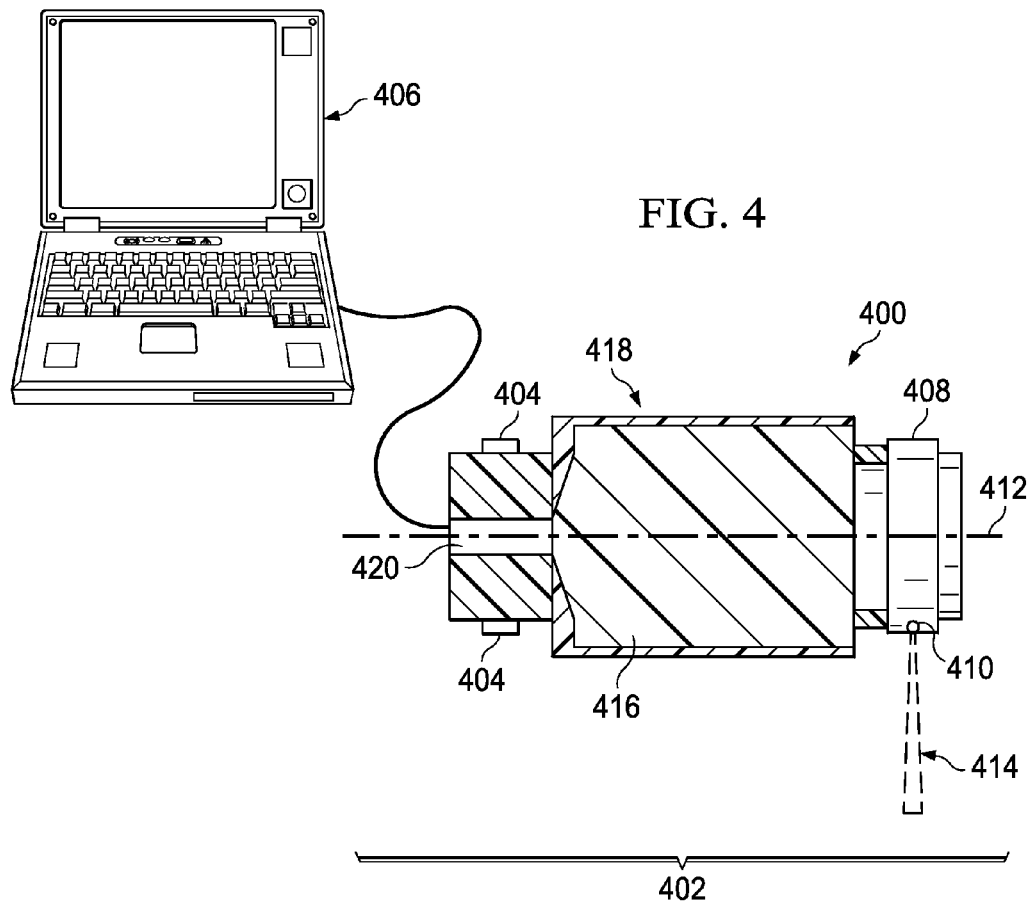
FIG. 4 depicts an illustration of a side view of an x-ray inspection tool in accordance with an advantageous embodiment.
Figure 5:
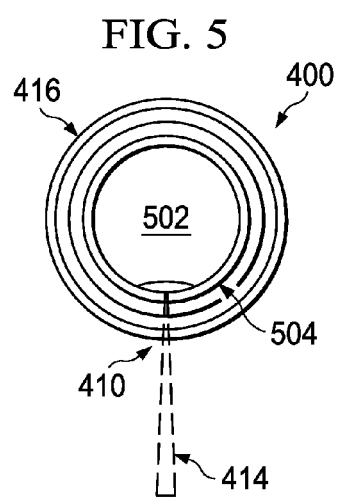
FIG. 5 depicts an illustration of a front view of an x-ray inspection tool in accordance with an advantageous embodiment.

FIG. 4 and FIG. 5 depict an illustration of two views of an x-ray inspection tool in accordance with an advantageous embodiment.

With reference now to FIG. 4, an illustration of a side view of an x-ray inspection tool is depicted in accordance with an advantageous embodiment. X-ray inspection tool 400 is an example implementation of x-ray inspection tool 202 in FIG. 2.

X-ray inspection tool 400 contains housing 402. Housing 402 contains imaging system 404. In this advantageous embodiment, imaging system 404 consists of two visible light cameras. Imaging system 404 is an example implementation of imaging system 214 in FIG. 2. Imaging system 404 provides imaging data to data processing system 406 to assist an operator in positioning X-ray inspection tool 400.

Housing 402 also contains cover 408. Cover 408 rotates around longitudinal axis 412. Longitudinal axis 412 is an example implementation of longitudinal axis 228. Cover 408 rotates around longitudinal axis 412 to a desired direction. X-ray inspection tool 400 then generates x-rays 414, which travel through hole 410.

X-rays that are reflected back to x-ray inspection tool 400 are received by x-ray detector 416. X-ray detector 416 is a scintillator in this advantageous embodiment. X-ray detector 416 is covered in plastic coating 418 in this advantageous embodiment for durability of x-ray detector 416. Light sensor 420 is also a component of x-ray detector 416 in this advantageous embodiment. Light sensor 420 identifies the light generated by x-ray detector 416 in response to being contacted by x-rays 414.

Turning now to FIG. 5, an illustration of a front view of an x-ray inspection tool is depicted in accordance with an advantageous embodiment.

In this advantageous embodiment, x-ray inspection tool 400 contains x-ray tube 502. X-ray tube 502 generates x-rays 414 by colliding high velocity electrons into anode 504. X-rays 414 then travel through hole 410.

Figure 6:
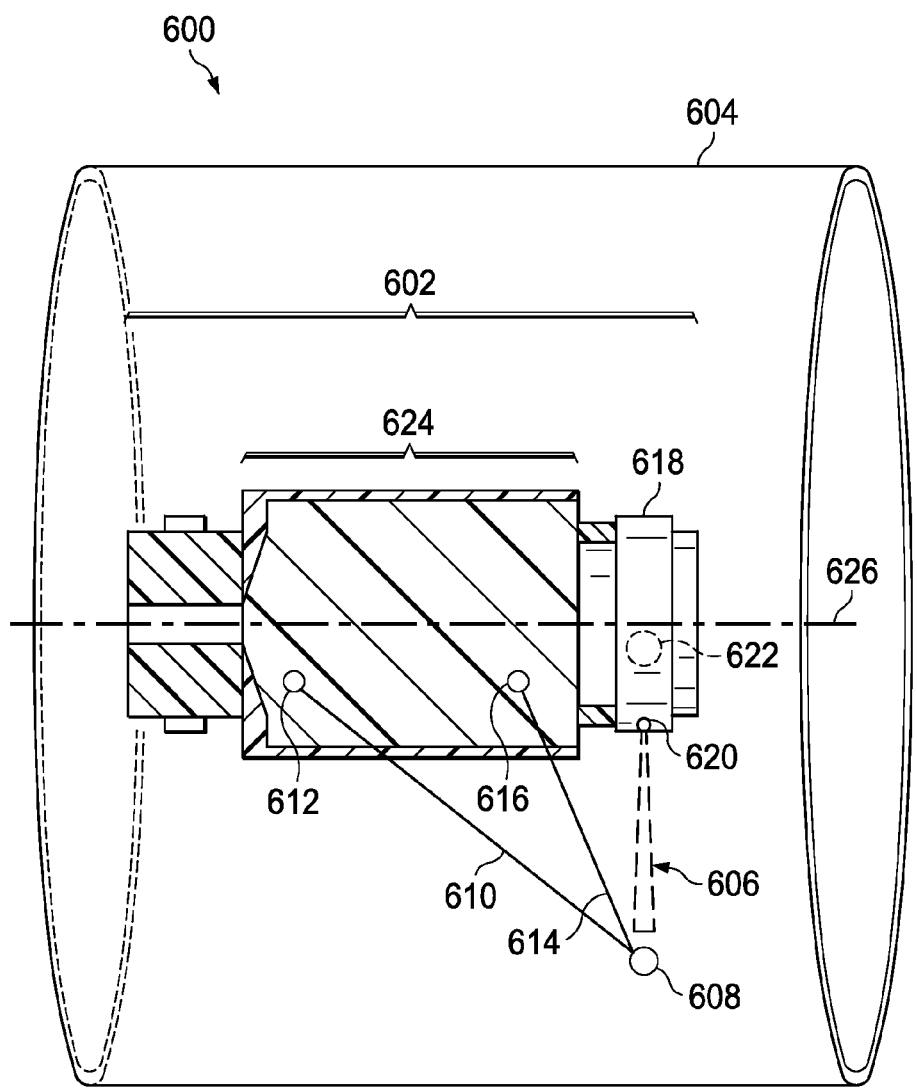
FIG. 6 depicts another illustration of an x-ray inspection environment in accordance with an advantageous embodiment.

Looking now to FIG. 6, another illustration of an x-ray inspection environment is depicted in accordance with an advantageous embodiment. X-ray inspection environment 600 is an example implementation of x-ray inspection environment 200 in FIG. 2.

In this advantageous embodiment, x-ray inspection tool 602 is used to inspect fuel tank 604 for inconsistencies in the surface of fuel tank 604. X-ray inspection tool 602 is an example of x-ray inspection tool 202 in FIG. 2. X-ray inspection tool 602 generates x-rays 606 and directs x-rays 606 toward point 608 in fuel tank 604 using hole 620. Hole 620 is an example of hole 232 in FIG. 2.

X-rays 606 travel through hole 620 toward point 608. Once x-rays 606 arrive at point 608, x-rays 606 are scattered because fuel tank 604 is at least partially composed of metal and sealant. In this advantageous example, x-rays are reflected back toward x-ray inspection tool 602 along path 610 and path 614. The x-ray traveling along path 610 arrives at x-ray inspection tool 602 at point 612, and the x-ray traveling along path 614 arrives at x-ray inspection tool 602 at point 616. Points 612 and 616 are located on x-ray detector 624. X-ray detector 624 is an example of x-ray detector 218 in FIG. 2.

Once the x-rays arrive at points 612 and 616, x-ray detector 624 identify that x-rays have been received along x-ray detector 624. X-ray inspection tool 602 then transmits the identification to a data processing system, such as data processing system 206 in FIG. 2.

In some advantageous embodiments, x-ray inspection tool 602 rotates cover 618 such that hole 620 is rotates to point 622. X-ray inspection tool 602 may then generate x-rays and direct the x-rays toward fuel tank 604 and receive x-rays that are scattered and return to x-ray detector 624. X-ray inspection tool 602 may rotate hole 620 to any direction along axis 626 by rotating cover 618.

Turning now to FIG. 7, a flowchart of a process for identifying a response to a plurality of x-rays is depicted in accordance with an advantageous embodiment. The process may be performed by x-ray inspection tool 202 in FIG. 2.

The process begins by generating the plurality of x-rays (operation 702). The plurality of x-rays may be generated by an x-ray tube, such as x-ray tube 212 in FIG. 2. The process then rotates an anode around a longitudinal axis to a direction (operation 704). The direction may be in a plurality of directions. Each direction in the plurality of directions may be a particular number of degrees from the next direction in the plurality of directions. In other words, the direction may be a predetermined stop in a circle.

The process then directs the plurality of x-rays toward a surface of an object in the direction (operation 706). In some advantageous embodiments, a hole in a cover that rotates with the anode inhibits x-rays not traveling in the direction from traveling outside the x-ray inspection tool. As used herein, inhibits means to prevent from traveling through an object. Thus, in this advantageous embodiment, a hole in the cover that rotates with the anode prevents the x-rays not traveling in the direction from traveling through the hole.

The process then identifies the response to the plurality of x-rays reflected from the surface of the object (operation 708). In some advantageous embodiments, the process sends the response received to a data processing system. The data processing system may use the response to generate an image. The process terminates thereafter.

Looking now to FIG. 8, a flowchart of a process for identifying an inconsistency in a surface of an object is depicted in accordance with an advantageous embodiment. The process may be performed by x-ray inspection tool 202 in x-ray inspection environment 200.

The process begins by turning on the x-ray testing tool and the data processing system connected to the x-ray testing tool (operation 802). The process then configures system parameters (operation 804). The system parameters may include the frequency with which images are generated and the amount of time between generating each image.

The process then moves the x-ray testing tool into the desired position (operation 806). In these examples, a human operator positions the x-ray testing tool. However, the x-ray testing tool may have a motor or other propulsion system that moves the x-ray testing tool automatically.

The process then rotates the cover and anode to a desired direction (operation 808). The process then turns on the x-ray tube and the x-ray detector (operation 810). The process then receives x-rays reflected from the surface using an x-ray detector (operation 812).

The process sends an indication of the x-rays received by the x-ray detector to a data processing system (operation 814). Next, the process rotates the cover and anode to the next direction in the index of possible directions for the cover and anode (operation 816). The process terminates thereafter.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

For example, the process may continue to generate x-rays and receive x-rays reflected from a surface of an object after operation 816. In such an advantageous embodiment, the process may continue to generate and receive x-rays until an event occurs. The event may be the expiration of a period of time, a number of images, or a number of directions for the anode and/or cover. Additionally, in these examples, the x-ray testing tool is positioned by a human operator in the object and near the surface. However, in other advantageous embodiments, a robotic arm may be used to position the x-ray testing tool or the x-ray testing tool may have a propulsion system, such as a motor.

Thus, the different advantageous embodiments allow an operator to test and identify inconsistencies in an area where other x-ray equipment may not physically fit. By using x-ray backscattering and using a flexible x-ray detector wrapped around the housing of the tool, the different advantageous embodiments allow the tool to be positioned in small areas that do not have a large external access and/or may not be disassembled.

The different advantageous embodiments provide cost and time savings because systems may be tested for inconsistencies without performing any disassembly. Additionally, some items to be tested may not be disassembled because the items are a single piece. For example, a pipe is a single piece that may not be disassembled.

The different advantageous embodiments also provide imaging data that is easy for an operator to interpret because the data processing system generates a flat image from the helical image data. The flat image data allows the operator to gain a sense of orientation for the location of the tool, which increases the ease of use of the tool as compared with an operator viewing and manipulating helical image data.

Thus, the different advantageous embodiments provide a method and apparatus for identifying a response to a plurality of x-rays. In one advantageous embodiment, an apparatus comprising a housing, an x-ray tube, an anode, and an x-ray detector are provided. The housing has a longitudinal axis. The x-ray tube is associated with the housing and configured to generate a plurality of x-rays. The anode is associated with the housing and configured to rotate around the longitudinal axis to a direction and direct the plurality of x-rays generated by the x-ray tube toward a surface of an object in the direction. The x-ray detector is associated with the housing and configured to detect a response to the plurality of x-rays reflected from the surface of the object.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
    a housing having a longitudinal axis;
    an x-ray tube associated with the housing and configured to generate a plurality of x-rays;
    an anode associated with the housing and configured to rotate around the longitudinal axis to a direction and direct the plurality of x-rays generated by the x-ray tube toward a surface of an object in the direction; and
    an x-ray detector wrapped around a circumference of at least a portion of the housing and configured to identify a response to the plurality of x-rays reflected from the surface of the object.

2. The apparatus of claim 1 further comprising:
    a cover associated with the anode having a hole configured to pass the plurality of the x-rays directed by the anode in the direction.

3. The apparatus of claim 2, wherein the direction is a first direction, and wherein being configured to pass the plurality of the x-rays directed by the anode in the first direction, the cover is configured to inhibit a subset of the plurality of x-rays traveling in a second direction.

4. The apparatus of claim 1, wherein the x-ray detector is flexible.

5. The apparatus of claim 4, wherein the x-ray detector comprises an organic material.

6. The apparatus of claim 1, wherein the x-ray detector comprises a scintillator, wherein the scintillator generates light in response to receiving the response.

7. The apparatus of claim 1, wherein the x-ray detector comprises a diamond coated material.

8. The apparatus of claim 1 further comprising:
    an imaging system associated with the housing and configured to generate imaging data of an environment.

9. The apparatus of claim 8 further comprising:
    a data processing system configured to receive the imaging data and information about the response.

10. The apparatus of claim 9, wherein the imaging data is first imaging data, and wherein the data processing system is further configured to generate second imaging data using the information about the response.

11. The apparatus of claim 10, wherein the second imaging data comprises a helical image.

12. The apparatus of claim 11, wherein the data processing system is further configured to generate a flat image using the helical image.

13. The apparatus of claim 1, wherein the x-ray detector has a channel and wherein the x-ray tube is located within the channel.

14. A method for identifying a response to a plurality of x-rays comprising:
   generating the plurality of x-rays;
   rotating an anode around a longitudinal axis to a direction;
   directing, by the anode, the plurality of x-rays toward a surface of an object in the direction; and
   identifying the response to the plurality of x-rays reflected from the surface of the object by an x-ray detector wrapped around at least a portion of the longitudinal axis.

15. The method of claim 14 further comprising:
   passing the plurality of the x-rays directed by the anode in the direction through a hole in a cover associated with the anode.

16. The method of claim 15, wherein the direction is a first direction, and wherein the step of passing the plurality of x-rays directed by the anode through the hole in the cover associated with the anode comprises:
   inhibiting a subset of the plurality of x-rays traveling in a second direction.

17. The method of claim 14, wherein the x-ray detector is flexible.

18. The method of claim 14, wherein the x-ray detector comprises an organic material.

19. The method of claim 18, further comprising:
   generating, by the x-ray detector, light in response to receiving the response.

20. An apparatus comprising:
   a housing having a longitudinal axis and configured to travel along a surface;
   an x-ray tube associated with the housing and configured to generate a plurality of x-rays;
   an anode associated with the housing and configured to rotate around the longitudinal axis to a direction and direct the plurality of x-rays generated by the x-ray tube toward the surface in the direction;
   a hole associated with the housing, wherein the hole rotates with the anode around the longitudinal axis and passes the plurality of x-rays directed by the anode in the direction; and
   an x-ray detector wrapped around a circumference of at least a portion of the housing and configured to identify a response to the plurality of x-rays reflected from the surface.

* * * * *